United States Patent [19]
Theisgen et al.

[11] Patent Number: 5,882,464
[45] Date of Patent: Mar. 16, 1999

[54] CONTINUOUS PROCESS FOR THE MANUFACTURE OF AN ABSORBENT CORE

[75] Inventors: Mario Matthias Theisgen, Mechernich/Eiserfey; John Christian Schmitt, Euskrichen-Kirchheim, both of Germany

[73] Assignee: The Procter & Gamble Co., Cincinnati, Ohio

[21] Appl. No.: 765,847

[22] PCT Filed: Jun. 20, 1995

[86] PCT No.: PCT/US95/07664

§ 371 Date: Dec. 19, 1996

§ 102(e) Date: Dec. 19, 1996

[87] PCT Pub. No.: WO95/35206

PCT Pub. Date: Dec. 28, 1995

[30] Foreign Application Priority Data

Jun. 22, 1994 [EP] European Pat. Off. .............. 94109595

[51] Int. Cl.[6] ...................................................... B32B 31/00
[52] U.S. Cl. .......................... 156/269; 156/301; 156/302; 156/467

[58] Field of Search .................................. 428/74, 78, 189, 428/190; 604/378, 385.1; 156/467, 552, 301, 302, 269

[56] References Cited

U.S. PATENT DOCUMENTS

| | | | |
|---|---|---|---|
| 3,661,680 | 5/1972 | Gore | 156/467 |
| 4,327,729 | 5/1982 | King | 128/287 |
| 4,861,652 | 8/1989 | Lippert et al. | 604/383 |
| 4,888,231 | 12/1989 | Angstadt | 428/213 |
| 5,399,240 | 3/1995 | Graef et al. | 162/9 |

*Primary Examiner*—James J. Bell
*Attorney, Agent, or Firm*—Matthew P. Fitzpatrick; Jeffrey V. Bamber; Steven W. Miller

[57] ABSTRACT

Absorbent articles having absorbent cores comprising multiple absorbent layers which are joined to each other. In particular, absorbent structures which have one of the absorbent layers being shorter in the manufacturing direction than at least one of the other layers and which are joined to one of the other layers by crimping and a process of crimping of a central patch of a fibrous web to a tissue.

2 Claims, 2 Drawing Sheets

CONTINUOUS PROCESS FOR THE MANUFACTURE OF AN ABSORBENT CORE

FIELD OF THE INVENTION

The present invention relates to absorbent articles having absorbent cores comprising multiple absorbent layers which are joined to each other. In particular the present invention relates to absorbent structures which have one of the absorbent layers being shorter in manufacturing direction of the absorbent articles than at least one of the other layers and which are joined to at least one of the other layers by crimping. The present invention also relates to a process of crimping of a central patch of a fibrous web to a tissue to replace previously necessary adhesive and the respective process to make such absorbent structures or embodiments of the present invention.

BACKGROUND OF THE INVENTION

U.S. Pat. No. 3,661,680 discloses a process for making an absorbent core comprising a layered construction of tissue, airfield and tissue. The process is indicated to combine the absorbent core by pressure rolls, however, by crimping along selected longitudinal lines. No cross-linked fibers and no super absorbent polymers are mentioned.

EP-A-593 relates to pad integrity improvements by use of a selected tissue which is placed between fibrous pads. Therefore this is the closest prior art for the basic core construction according to the present invention. However only compression to density but no crimping to join the fibrous pads to the tissue is mentioned.

EP-A-21662 relates to a wicking improvement by use of a special pattern of embossing a fibrous core to a tissue. However, no benefit for the core integrity is indicated and the process to make the absorbent core construction does not mention crimping but shows a patterned compression roll.

EP-A-214190 discloses the crimping of multiple layers of tissue to immobilize particles trapped between the layers. The basic principle of longitudinal crimping lines also is disclosed however no cross-linked fibrous patch is mentioned.

EP-A-214867 discloses fibrous structures with embossed wicking lines. This is not related to core integrity but to the placement of the structure within the product. No crimping of tissue to fibrous material is mentioned and no cross-linked fibers are disclosed.

EP-A-399564 discloses wicking improvements due to the selective density of webs of cross-linked cellulose. Densification by calendering is disclosed however no mention of tissue to pad crimping or core integrity improvements are discussed.

When making absorbent articles it is desirable to have discontinuous patches of absorbent patches disposed on continues bands of absorbent material, e.g. tissue. This is particularly true for the highly effective but expensive cross linked fibers now starting to be used more and more in the industry. In particular when using high speed machinery the discontinuous patches have to be joined to the continuous bands or else it would not be possible to transport them. This has typically been done by gluing the patches to the tissue.

However, the leading and trailing ends of a patch are problematic to be glued due to on off characteristics of the glue delivery and application equipment, it also may cause manufacturing efficiency losses due to glue contamination. Therefore patches were often only glued to the tissue in their center leaving the leading and trailing ends without attachment to the tissue. This however then easily leads to flying patches during production, even further reducing productivity. All these problems are even aggravated if the process of making absorbent cores includes a turning point where the band of already combined material is turned upside down, which has been found useful in obtaining particular products.

Therefore the problem underlying the present invention is to provide an absorbent core comprising a first absorbent structure, a tissue and a second fibrous absorbent structure which is shorter than the tissue in one direction and otherwise not extending beyond the periphery of the tissue. The tissue being joined to the second absorbent structure by crimping.

Preferably the crimping is done along one or several discrete lines. Even so not necessary for the present invention it is preferred if the interface between tissue and the second absorbent structure is free of adhesives.

An additional aspect of the present invention is a continuous process for the manufacture of absorbent cores according to the above description, comprising the steps of placing a continuous tissue on a conveyer belt; forming and depositing in discrete sequence a second fibrous absorbent structure on the continuous tissue; joining the tissue and the second fibrous absorbent structure to each other by crimping; forming the first absorbent structure as a continuous band and placing it onto the tissue on the opposite side from where said first fibrous structure is placed and finally severing the continuous band of tissue and first absorbent structure between one and the following of the second absorbent structures.

SUMMARY OF THE INVENTION

The present invention relates to an absorbent core extending along a first axis and perpendicular thereto along a second axis and being produced in the direction of the first axis. The absorbent core comprises a first absorbent structure which has the same first and second axis as the absorbent core, a tissue and a second absorbent structure. The tissue has a first and a second surface and has substantially the same length as the first absorbent structure along the first axis.

The second absorbent structure is shorter than the tissue along the first axis and does not extend beyond the periphery of the tissue in direction of the first axis, preferably in any direction. The second absorbent structure usually is a fibrous absorbent structure preferably comprising cross-linked fibers.

The first absorbent structure can be selected from a variety of absorbent structures but preferably also comprises fibers in particular in combination with polymer absorbent gelling material most preferably in particulate form. These absorbent gelling materials may also be present in the second absorbent structure.

The first absorbent structure is contiguous with the first surface of the tissue and is coextensive along the first axis with that tissue. The absorbent core is constructed such that the tissue on its second surface and the second absorbent structure are joined to each other by crimping.

In the preferred embodiments according to the present invention the second absorbent structure does not extend to the periphery of the tissue at all. However the crimping extends along the first axis at least to one end of the second absorbent structure preferably the crimping extends along the first axis to both ends of the second absorbent structure and for simplicity of manufacturing it is most preferred that the crimping is continuous thereby extending along the fill length of the tissue along the first axis.

The crimping may form one of several discrete lines along the first axis and preferably is used to replace adhesive on the second surface on the tissue in order to prevent clogging of the surface by adhesive, improve the manufacturing by elimination of glue heating, glue delivery and application equipment and the problems associated with the required on-off cycling of glue applications.

Accordingly the present invention also relates to a continuous process for the manufacture of the absorbent core of the present invention. This process comprises the steps of placing a continuous tissue on a conveyor belt;

forming and depositing in discrete sequence second fibrous absorbent structures on the second side of the tissue;

joining the tissue and the second absorbent structure to each other by crimping;

forming the first absorbent structure as a continuous band and placing it on the first side of the tissue;

severing the continuous band of tissue and first absorbent structure between one and the following of the second absorbent structure.

The absorbent core according to the present invention can be used in all kinds of absorbent products particularly in disposable absorbent diapers for babies, children or adults as well as in incontinence inserts or in sanitary napkins.

DETAILED DESCRIPTION OF THE INVENTION AND THE DRAWINGS

Figure 1:
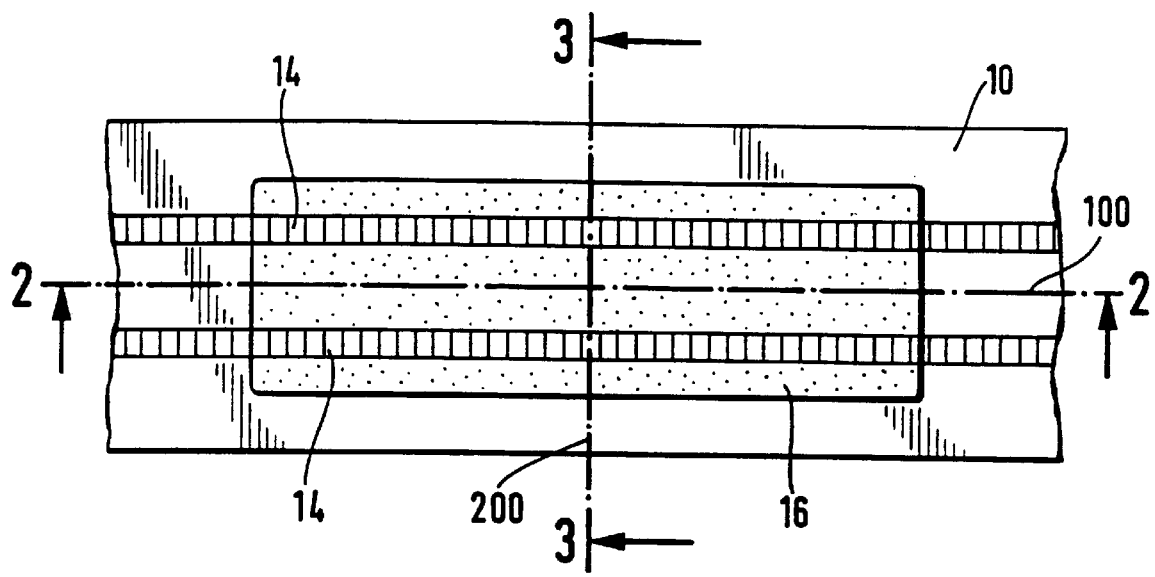
FIG. 1 shows a top plan view of a tissue continuously crimped to a second absorbent fibrous structure.
Figure 2:
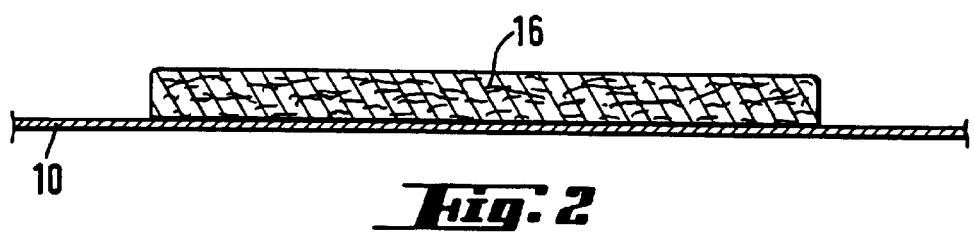
FIG. 2 is a cross sectional view of the embodiment of the invention of FIG. 1 along line 2/2.
Figure 3:
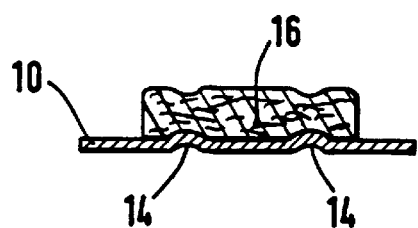
FIG. 3 is a cross sectional view of the embodiment of the invention of FIG. 1 along the line 3/3.

FIG. 1 shows a continuous tissue (10) having a first axis (100) and perpendicular thereto a second axis (200). The tissue is overlying a second absorbent structure (16) sharing the axis (100) and (200) with the tissue (10). The tissue (10) and the second absorbent structure (16) are joined by crimping lines (14). The direction of movement during manufacturing is parallel to the first axis (100). When looking at a cross section of this part of the core according to the invention in FIG. 2 it can be seen that the second absorbent structure (16) is placed on the second surface of the tissue (10) and joined along the crimping line (14) to that tissue. Not shown in the Figures but part of the absorbent cores of the present invention is a continuous first absorbent structure which is placed on the first side, i.e. the opposite side than the second side, of the tissue (10).

In an alternative cross section along line 3—3 of FIG. 1 the crimping lines (14) at which the second absorbent structure (16) and the tissue (10) are compressed together in a crimping process can be seen.

Figure 4:
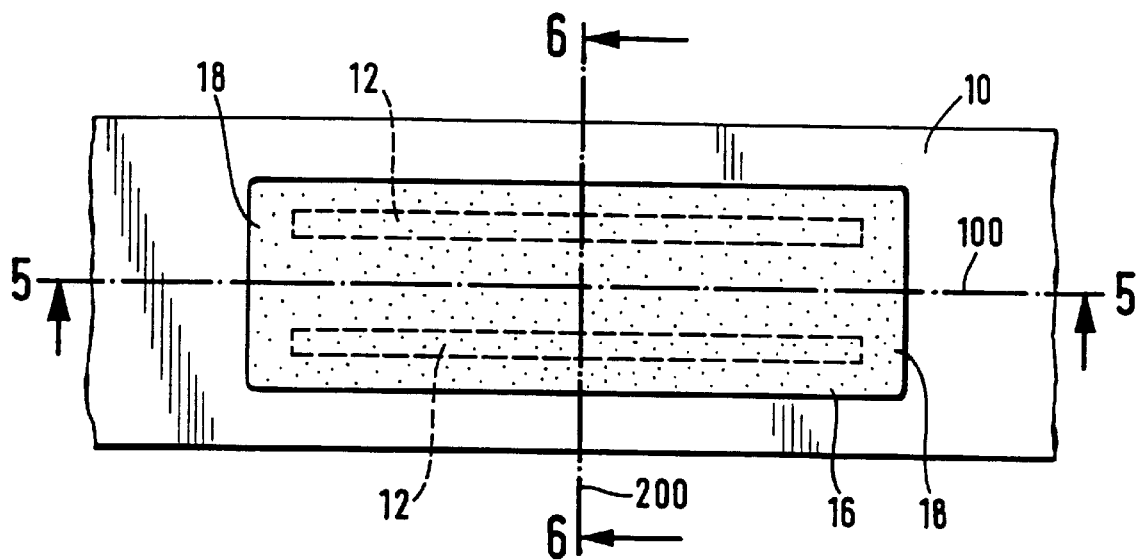
FIG. 4 is a top plan view of a prior art tissue and second absorbent fibrous structure glued to each other.

FIG. 4 shows a prior art structure also having a first axis (100), a second axis (200) of a tissue (10) and a second absorbent structure (16). However, in this prior art embodiment the joining between the second absorbent structure (16) and the tissue (10) is provided by adhesive lines (12) leaving non-adhered ends (18) between the second absorbent structure (16) and the tissue (10).

Figure 5:
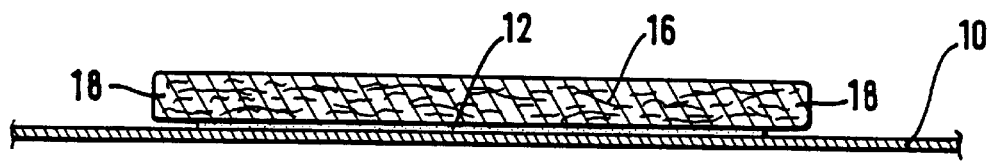
FIG. 5 is a cross sectional view of the prior art embodiment of FIG. 4 along line 5/5.
Figure 6:
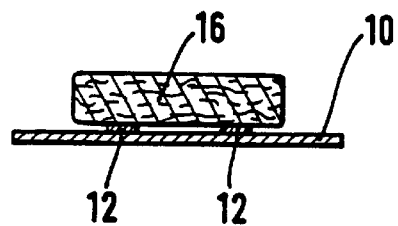
FIG. 6 is a cross sectional view of the prior art embodiment of FIG. 4 along line 6/6.

As can be seen from FIG. 5 the non-adhered ends (18) of the second absorbent structure (16) would easily lift up from the tissue (10) when the tissue is moved in a direction parallel to the first axis (100). Also the width/length of the adhesive lines (12) should be considered since liquid deposited on one side of the absorbent core may have to communicate through the plane where the adhesive prevents such communication across the width and length of the adhesive lines (12).

As used herein the term "disposable absorbent articles" refers to articles which absorb and contain body exudates and more specifically refers to articles which are placed against or in the proximity of the wearer's body to absorb and contain the various exudates discharged from the body of the wearer and which are not intended to be laundered or otherwise restored or reused as an absorbent article (i.e. they are intended to be discarded after a single use and, preferably to be recycled, composted or otherwise disposed of in an environmentally compatible manner). Embodiments of the disposable absorbent article of the present invention are adult incontinence briefs or baby, children's diapers. Examples of the kind of diapers to which the present invention is readily adapted are shown in U.S. Pat. No. RE 26,151; U.S. Pat. No. 3,860,003; 4,253,461; and 7,704,115.

In general absorbent cores according to the present invention are useful in all disposable absorbent articles.

As used herein the term "absorbent core" refers to all absorbent means in a disposable absorbent article. According to the present invention absorbent cores comprise a first and a second absorbent structure separated by a tissue there between. However further absorbent layers may be comprised in the absorbent cores if deemed appropriate for the particular use of the absorbent article.

In the following reference will be made often to absorbent diapers which however should not mislead in that sanitary napkins, catamenials, panty liners or incontinence inserts represent possible end products in which the absorbent structures according to the present invention may be utilized.

The outside surface of a diaper usually is the surface farthest from the wearer during use of the diaper. The backsheet preferably forms most of the outside surface. The inside surface is that surface of the diaper opposite the outside surface and is preferably formed by the topsheet. Preferably, the inside surface of the diaper is coextensive with the outside surface and in general the inside surface is for the greater part in contact with the wearer when the diaper is used. Typically the outside surface and the inside surface include the absorbent core such that the topsheet and the backsheet extend beyond the core periphery and are joined to each other.

The first and second absorbent structure of the present invention may comprise any absorbent means which ate generally compressible, comformable, non-irritating to the wearer's skin, and capable of absorbing and retaining liquids such as urine menses and other body exudates. The absorbent structure may be manufactured in a wide variety of sizes and shapes (e.g., rectangular, hourglass, asymmetric, T-shaped, etc.) and from a wide variety of liquid absorbent materials commonly used in disposable absorbent articles such as communited wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials or any equivalent materials or combination of materials. The configuration and construction of the absorbent core may also be varied e.g., the absorbent core may have varying caliper zones, a hydrophillic gradient, a superabsorbent gradient (as in concentration or particle size for granular superabsorbents), or lower average density and lower average basis weight aquisition zones; or may comprise one or more layers or structures. The total absorbent capacity of the absorbent core should, however, be compatible with the design exudate loading and the intended use of the core.

A preferred embodiment of a diaper has an hourglass-shaped absorbent core. An exemplary absorbent structure readily adaptable for use in the absorbent core of the present invention is described in U.S. Pat. No. 4,610,678 4,673,402 4,888,231. The absorbent core may also be adapted from the commercially successful absorbent member described in U.S. Pat. No. 4,834,735 entitled "High Density Absorbent Members Having Lower Density and Lower Basis Weight Aquisition zones". Other preferred absorbent cores are described in U.S. Pat. Nos. 4,685,915 and 4,781,710 as comprising fibrous structures having areas of different absorbent capacity, density, or liquid acquisition speed. An alternative thin absorbent core useful in the present invention may be found in U.S. Pat. No. 4,600,458. Another preferred absorbent core design provides for a cross linked cellulose patch essentially without superabsorbent on top of an airfelt with superabsorbent mixture comprising more than 30% superabsorbent.

Preferably the second absorbent structure comprises cross-linked fibers, in particular cross-linked cellulose fibers. In general the first and the second absorbent structures can comprise the same absorbent materials which can be any of those known in the art. The difference between the first and the second absorbent structure according to the invention will be depending on the adaptation of the respective structure to the particular function in the context of the specific absorbent article for which the absorbent core is designed for.

The tissue used between the first and the second absorbent structure according to the invention can be any kind of crimpable tissue usual in the art. Typically tissues comprising wood pulp fibers are used but the tissue fibers may comprise synthetic fibers as well as natural fibers or the tissue may even be a laminate in itself comprising several layers of various tissue type materials or even a laminate structure which comprises particulate materials like for example super absorbent polymers between layers.

The absorbent core is superposed on the backsheet and is preferably joined thereto by a core attachment means. The backsheet is impervious to liquids (e.g. urine) and is preferably manufactured from a thin plastic film, preferably a thermoplastic film, although other flexible liquid impervious materials may also be used. As used herein, the term "flexible" refers to materials which are compliant and which will readily confirm to the general shape and contours of the human body. The backsheet prevents the exudates absorbed and contained in the absorbent core from soiling articles which contact the diaper such as bedsheets and undergarments.

The backsheet may thus comprise polymeric films such as thermoplastic films of polyethylene or polypropylene, or composite materials such as a film-coated nonwoven material. For economic, aesthetic, and ecological reasons, the backsheet preferably has an average nominal caliper, i.e. calculated caliper, of less than about 0.051 mm, more preferably a calculated caliper of from 0.020 mm to 0.036 mm. Preferably, the backsheet is a flexible polyethylene film. Exemplary films for use as the backsheet of the present invention are manufactured by Tredegar Industries, Inc. of Terre Haute, Ind., USA or BP-Chemical PlasTec Rotbuchenstrasse 1, D-8000 MÜNCHEN, Germany.

The topsheet forming the inside surface of the absorbent article is compliant, soft feeling, and non-irritating to the wearer's skin. Further, the topsheet is liquid pervious permitting liquids (e.g. urine) to readily penetrate through its tickness. A suitable topsheet may be manufactured from a wide range of materials, such as porous foam, reticulated foams, apertured films; or woven or nonwoven webs of natural fibers (e.g. wood or cotton fibers), synthetic fibers (e.g. polyester or polypropylene fibers) or from a combination of natural and synthetic fibers. Preferably, it is made of a material that isolates the wearer's skin from liquids retained in the absorbent core.

The diaper preferably further comprises one or several elasticized leg cuffs for providing improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs). U.S. Pat. No. 3,860,003 entitled "Contractable Side Portions for a disposable diaper" describes a disposable which provides a contractible leg opening having a side flap and elastic members to provide an elasticized leg cuff (gasketing cuff). U.S. Pat. No. 4,909,803 entitled "Disposable absorbent article having elasticized flaps" describes a disposable diaper having "stand-up" elasticized flaps (barrier cuffs) to improve the containment of the leg regions. U.S. Pat. No. 4,695,278 entitled "Absorbent article having dual cuffs" describes a disposable diaper having dual cuffs including a gasketing cuff and a barrier cuff. U.S. Pat. No. 4,704,115 entitled "Disposable waist Containment garment" discloses a disposable diaper or incontent garment having side-edge-leakage-guard gutters configured to contain free liquids within the garment.

The diaper may also further comprise an elastic waist feature that provides improved fit and containment or any other features typically provided on diapers or incontinent garments as are known in the art.

The crimping according to the invention is usually conducted by applying high pressure between a hammer and an anvil role which compress the tissue and the second absorbent structure to form a localized high density pattern in which the tissue and the secondary absorbent structure fibers are pressed into each other such that their cohesive and adhesive force allows the second absorbent structure to be joined effectively to the tissue.

There are no particular requirements towards the pattern of the crimping. However since it is known that high density lines in an absorbent article may be beneficial for the liquid distribution in such an absorbent article and crimping lines represent lines of high density they may be formed such as to perform part or all of the liquid distribution function otherwise incorporated by separately formed high density lines in an absorbent core. The crimping lines may also be replaced by other patterns known to be beneficial for liquid distribution, asthetic consideration or otherwise.

For the crimping heated or cold crimping rolls can be used. The primary objective of the crimping is to ensure that the ends of the absorbent second structure are held to the tissue in order to not separate during manufacturing. If propperly made the crimping lines will however continue to hold the secondary absorbent structure to the tissue also during use of the absorbent article and hence improve core integrety without the need for other core adhesion means.

What is claimed is:

1. An absorbent core extending along a first axis and perpendicular thereto along a second axis, said absorbent being produced in the direction of said first axis, said core comprising:

(a) a first absorbent structure having the same first and second axis as said absorbent core;

(b) a tissue having a first and second surface and substantially the same length as said first absorbent structure along said first axis;

(c) a second absorbent structure having the same first and second axis as said absorbent core, being fibrous and being shorter than said tissue along said first axis, said second absorbent structure not extending beyond the periphery of said tissue in direction of said first axis;

said first absorbent structure being contiguous with said first surface of said tissue and co-extensive along said first axis with said tissue; wherein said absorbent core is constructed in a continuous process comprising the steps of (i) placing said tissue on a conveyor belt wherein said tissue is continuous on said conveyor belt;

(ii) forming and depositing in discrete sequence said second fibrous absorbent structures on said second side of said continuous tissue;

(iii) joining said tissue and said second structures by crimping;

(iv) forming said first absorbent structure as a continuous band and placing it on said first side of said tissue;

(v) severing the continuous band of tissue and first absorbent structure between one and the following of said second absorbent structure.

2. A continuous process according to claim 1 wherein said crimping is continuous between one and the following of said second fibrous absorbent structures.

* * * * *